(12) United States Patent  
Mannhardt et al.

(10) Patent No.: US 7,525,662 B2  
(45) Date of Patent: Apr. 28, 2009

(54) APPARATUS AND METHOD FOR ENVIRONMENTALLY ISOLATED ANALYSIS

(75) Inventors: Joachim Mannhardt, Eschach (DE); Trevor Page, Hamshire (GB); Martin Koch, Neuenburg (DE)

(73) Assignees: GEA Niro GmbH (DE); J&M Analytik AG (DE)

( * ) Notice: Subject to any disclaimer, the term of this patent is extended or adjusted under 35 U.S.C. 154(b) by 234 days.

(21) Appl. No.: 11/690,203

(22) Filed: Mar. 23, 2007

(65) Prior Publication Data

US 2007/0224853 A1 Sep. 27, 2007

(30) Foreign Application Priority Data

Mar. 23, 2006 (DE) .................... 10 2006 013 341

(51) Int. Cl.  
*G01N 21/00* (2006.01)

(52) U.S. Cl. ....................... 356/432; 356/436

(58) Field of Classification Search ......... 356/432–440, 356/241.1–241.6, 244, 246  
See application file for complete search history.

(56) References Cited

U.S. PATENT DOCUMENTS 7,382,458 B2 * 6/2008 Johnson et al. ............. 356/436

7,398,804 B2 * 7/2008 Koch et al. .................. 141/315  
2008/0212087 A1 * 9/2008 Mannhardt et al. .......... 356/244

FOREIGN PATENT DOCUMENTS

EP 1 441 953 B1 5/2003  
WO 03/037717 A1 5/2003

* cited by examiner

*Primary Examiner*—Hoa Q Pham  
(74) *Attorney, Agent, or Firm*—GrayRobinson, PA

(57) ABSTRACT

An apparatus for analyzing a product to be analyzed which is located in a receptacle provided with a coupling element, in particular for photometric or spectrophotometric analysis of powder, bulk material, granular material and similar, is provided with a docking element for sealing connection to the coupling element, and with a measuring probe which is arranged in a probe housing and is provided with at least one radiation and light measuring element, at least one measuring window, which is arranged in the beam path and is arranged in a wall of the probe housing, and with at least one detection element for the analysis. The probe housing with the measuring probe is designed and guided displaceably in such a way that at least a part of the probe housing in which the measuring window is located can be inserted into the receptacle for the analysis.

37 Claims, 3 Drawing Sheets

APPARATUS AND METHOD FOR ENVIRONMENTALLY ISOLATED ANALYSIS

FIELD OF THE INVENTION

The invention relates to the field of analyzing substances.

More particularly, the invention relates to an apparatus for the analysis, such as photometric or spectrophotometric analysis, of the contents of a receptacle of a type which is provided with a sealing coupling element fir environmentally isolating those contents. A further aspect of the invention relates to a method for the analysis of a substance to be analyzed while the substance is located in an environmentally isolated fashion in a receptacle.

BACKGROUND OF THE INVENTION

End products from one or more raw materials or raw products are produced in many industrial sectors such as, for example, the chemical, pharmaceutical or food processing industries. The raw products are mostly brought to the location or to the plant, in which the treatment and processing to form an intermediate product or end product is to take place, in receptacles such as sacks or else in firm containers, this being done in the form of bulk materials such as powder, granular material, fluid or similar.

However, substances such as these raw products are frequently present in a concentrated form which is damaging to the environment and/or health. For this reason, decanting or filling operations are carried out as far as possible so as to avoid contamination of the substance and/or the environment, and also to avoid health being endangered by the substance.

To this end, in EP 1 441 953 B1, for example, the receptacle in which the raw product is located is provided with a sealed docking device by means of which decanting or filling is carried out under so-called "total containment", an environmentally isolated sealing being maintained. In this case, the docking device comprises a first coupling element which is connected to the receptacle, and a second coupling element or a docking element, which is intended to provide a sealing connection to the receptacle and from which the raw product supplied is to be decanted or filled. In this case, decanting through an interconnection of the two receptacles or containers via the coupling elements is performed by virtue of the fact that each coupling element can be elastically deformed in such a way that connecting openings are cleared only for the decanting.

In addition to the filling and decanting operations which—as mentioned—are to take place in an environmentally isolated fashion, it is also frequently necessary to analyze the supplied product, for example to analyze its composition, concentration, the degree of purity and the like. For this purpose, it has therefore been necessary to open the receptacle, in which case samples were removed as far as possible without heavy contamination and environmental damage, such that it was possible subsequently to examine them in an analytical laboratory. However, it was not possible in the case of that method of analysis to reliably prevent contamination and/or escape or release of the product to be analyzed.

BRIEF SUMMARY OF THE INVENTION

It is an object of the present invention to provide an apparatus for the analysis of a substance which is located in an environmentally isolated receptacle, which apparatus can be used to carry out the analysis in such a way that environmental isolation or sealing from the environment is reliably maintained even in the case of requisite analyzes.

It is also an object of the invention to provide a method for the analysis of a substance which is located in an environmentally isolated receptacle, with the aid of which method the environmental isolation or sealing is maintained.

According to the invention, this object is achieved with the aid of an apparatus for analysis having the features named in claim 1.

Claim 31 recites a method for the analysis of the contents of a receptacle wherein the contents to be analyzed are located in an environmentally isolated fashion in a receptacle, which method can likewise be carried out while maintaining environmental isolation.

It is nevertheless possible to maintain "total containment" with the aid of the inventive apparatus and the method even in cases in which the delivered product has to be subjected to a further analysis.

Instead of removing a sample and conducting an external analysis in a laboratory, the inventive apparatus provided with a docking element is placed, via the same coupling element and while maintaining the sealing with its probe housing in which the measuring probe is arranged, in the receptacle that is otherwise used for decanting or filling the product.

When the product is being transported away again in large quantities in receptacles after having been treated or processed, the inventive apparatus can be used in the same way also to carry out a final quality control in addition to the previously mentioned incoming inspection when the receptacle in which the treated product is located is likewise correspondingly provided with a coupling element to which the inventive apparatus can then be connected with the aid of its docking element. In this case, as well, influencing of the environment and/or contamination of the treated product are reliably avoided.

If, in addition to the sealing by the coupling element and the docking element during the measuring method, it is desired to seal off yet more securely from the outside, it can be provided to arrange at least one further additional seal between the probe housing and the guide housing.

In an advantageous refinement of the invention, it can be provided that the at least one measuring window is arranged in at least one subregion of a circumferential wall of the probe housing.

If required, such an arrangement of one or more measuring windows renders it possible to carry out measurements over 360°, and/or various measuring methods for a respective specific region of the receptacle.

A further advantage of the arrangement of the at least one measuring window in a circumferential wall, for example a cylindrical circumferential wall of the probe housing consists in that upon retraction of the measuring probe from the receptacle the latter can be cleaned when passing the elastic coupling element and the docking element, if appropriate additionally also at a separate seal.

In a further advantageous refinement of the invention, it can be provided that there is located between a front end face of the probe housing and the measuring window arranged in the circumferential wall a sealing cap which, in a retracted position of the measuring probe in which the measuring window is located outside the receptacle, is at least partially still located in a region, cleared by the coupling element, of an opening in the interior of the receptacle, and therefore covers the opening.

Owing to the sealing cap, because of the sealing of the opening into the receptacle an intermediate position is provided in which it is possible to clean the regions of the measuring probe, in particular of the probe housing, which come into contact with the product before the apparatus is completely removed again.

Such a cleaning can be provided, for example, by a flushing device which has, for example, a flushing medium chamber which is arranged in an interspace between the probe housing and the guide housing at least in the region of the measuring window. To this end, the flushing medium chamber can correspondingly be provided with an inflow and at least one outflow for flushing medium.

Advantageous developments and refinements of the invention follow from the remaining subclaims and from the exemplary embodiment subsequently described in principle with the aid of the drawings, in which:

DETAILED DESCRIPTION OF A PREFERRED EMBODIMENT

Figure 1:
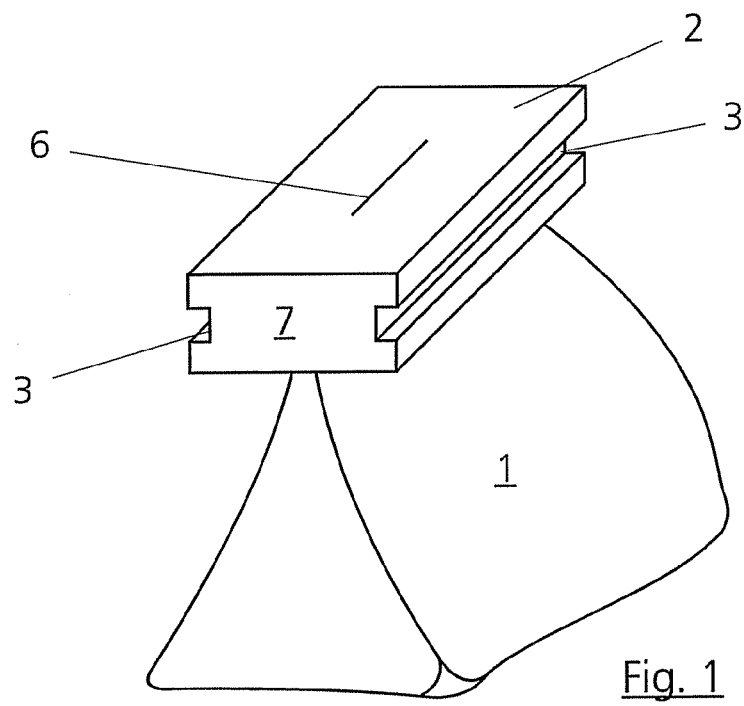
FIG. 1 is a perspective view of a receptacle of the type having a coupling element.
Figure 2:
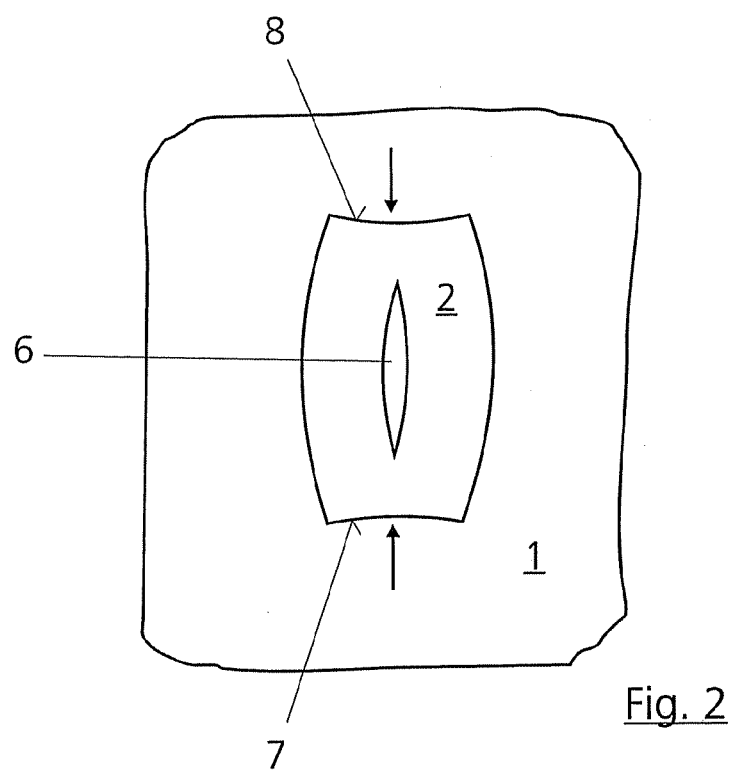
FIG. 2 is a top view of the coupling element according to FIG. 1 in the partly opened state.

A receptacle 1 illustrated in FIGS. 1 and 2 is provided with a coupling element 2. The structure and configuration of the coupling element 2 are disclosed in EP 1 441 953 B1, and so will be examined here only briefly. EP 1 441 953 B1 likewise constitutes a disclosure content relating to the present application and is expressly incorporated herein by reference in its entirety to form pat of the present disclosure as if fully set forth herein. As may be seen, the coupling element 2 is designed in the shape of an elastomeric body of elongated configuration, and has lateral guide grooves 3 into which it is possible for the purpose of connection to another container or another apparatus to push on a second coupling or docking element 4 (see FIGS. 3 to 5) having a mating profile in relation to the guide grooves 3, thus enabling a product located in the receptacle 1 to be removed or decanted. To this end, the docking element 4 has corresponding lateral edges 5 which are shaped such that they can be displaceably fitted into the grooves 3 of the coupling element 2. This type of connection, known per se, constitutes a type of dovetail connection and therefore produces a reliable and yet easily disconnectable connection. The coupling element 2 is provided between the two lateral surfaces with a slit 6 which is of continuous design from the top side to the bottom side and extends over a subregion of the length of the coupling element 2.

When the coupling element 2 is not exposed to any external forces, it is in its closed state, in which the slit 6 is likewise tightly sealed. In this closed state, the interior of the receptacle 1 with the product is sealed against the environment. In order to ensure yet more reliable sealing, and also to avoid inadvertently opening the slit 6 during transport or handling, it is additionally possible also to mount on the coupling element 2 a locking element by means of which the slit 6 can also additionally be sealed. EP 1 441 953 B1 describes such a locking element, for example. Instead of the locking element, the docking element 4 is then later pushed on for the method of analysis described in more detail below.

FIG. 2 shows the coupling element 2 in a partly opened state. This state results whenever a force is applied as illustrated in the directions of the arrows to the front side 7 and rear side 8 of the coupling element 2 which is appropriately of elastic design. When pressure is applied in this way the coupling element 2 is deformed correspondingly in such a way that the slit 6 opens to form a larger gap.

In order to maintain a seal, this opening operation by a corresponding application of pressure is, of course, carried out only when a second coupling element or, in the present case, the docking element 4 is correspondingly mounted. To this end, the docking element 4 is likewise designed as an elastomeric body having substantially the same dimensions as the coupling element 2. For the purpose of connection, the docking element 4 is appropriately pushed onto the coupling element 2 from one end, in which case, if appropriate, a locking element (not illustrated) located on the coupling element 2 is pushed down. The docking element 4 likewise has a slit 9 which corresponds in position and length to the slit 6. The docking element 4 is connected to the apparatus for analysis described in FIGS. 3 and 5.

The apparatus has a measuring probe 10 having a probe housing 11 which is provided with various devices for the analysis of the product to be analyzed, which is located in the receptacle 1. Of course, it is possible for any other type of container to be provided instead of a sack-like receptacle 1. All that is essential is a coupling element 2 on the receptacle 1 which is compatible with the docking element 4. The measuring probe 10 is sealed to the outside by a guide housing 12, for example a closed cylindrical guide, and a sealing ring 13 which is arranged in the rear end wall of the guide housing 12. The guide housing 12 simultaneously also constitutes a guide for the probe housing 11, and thus for the measuring probe 10. The probe housing 11 and the guide housing 12 are of cylindrical design, and the measuring probe 10 can be displaced, together with the probe housing 11, in an axial direction with respect to the guide housing 12, as a result of which it can dip into the interior of the receptacle 1, as is described below in more detail.

In principle, the structure of the measuring probe 10 is of known design, for which reason only the parts which are important for the invention are described in more detail below.

Arranged in the interior of the measuring probe 10 are, for example, a number of transmitting light guides 14 arranged uniformly distributed over the circumference, and one or more receiving light guides as detection elements 15. In this case, each light guide can, if required, also comprise a combination of a number of light guides or be a bundle of light guides, in order to carry out the various known measuring methods such as, for example, Raman, Fluorescence, LIF, LIBS. Various combinations of measuring methods with different light guide configurations can also be carried out, such as measurements in reflection and fluorescence measurements, depending on the configuration of the light guides. If appropriate, the associated light guides are coupled for this purpose to corresponding detectors (not illustrated). The transmitting and receiving light guides 14 and 15, respectively, are provided in a known way with connections via which a connection to a test and evaluation unit, not illustrated in detail, is made.

One or more measuring windows 16 are arranged in the circumferential wall of the probe housing 11 in the front region, dipping into the receptacle 1, of the probe housing of the measuring probe 10. 360° measurements are possible when the measuring window 16 extends in an annular shape over the entire circumference of the probe housing 11. A material which is resistant to aggressive media, such as sapphire or quartz, for example, is to be used as material for the measuring window or windows 16. For an end termination of the probe housing 11, the measuring window or windows 16 is or are adjoined by a sealing cap 17 which is tightly connected to the measuring window or windows 16 and to the rest of the probe housing 11 in a way not illustrated in detail, so as to produce a seal. A screw connection (not illustrated) with sealing elements can, for example, be provided as fastening. If required, a temperature sensor (not illustrated) can also be arranged in sealing cap 17 in order to measure the temperature in the interior of the receptacle 1 with the product to be analyzed.

In order to deflect the beams generated by the transmitting light guide or guides 14, a radiation deflecting device in the form of one or more deflecting mirrors 18 is arranged in the interior of the measuring probe 10 in the region of the measuring window or windows 16. The deflecting mirrors 18 can, for example, be aligned in such a way that they are distributed over the circumference at an angle of 45° to the longitudinal axis of the measuring probe 10 and of the probe housing 11, so that the axially incident beams can be deflected in a radial direction, and in this way can emerge radially from the measuring window or windows 16, and the product to be analyzed can thereby be appropriately analyzed. The deflecting mirrors 18 also serve simultaneously to deflect radiations reflected in the interior of the receptacle and further measured values, which are returned via the receiving light guide or guides 15 to the evaluation unit (not illustrated).

Instead of a number of mirrors arranged distributed over the circumference, a mirror unit in the shape of a cone, the shape of a conical frustum or the shape of a pyramid can also be used corresponding reflecting surfaces being provided. If a number of measuring windows 16 or a measuring window 16 which extends over 360° is or are used, a combination of different measuring methods can be carried out simultaneously in conjunction with a number of mirrors 18 or reflecting surfaces when a corresponding number of receiving light guides 15 are provided.

If required, a multiplicity of transmitting light guides or receiving light guides 14 and 15 can be provided for a great variety of measurements and analyzes in the interior of the probe housing 11. Thus, for example, it is possible to provide six transmitting light guides 14 arranged distributed over the circumference, and one central receiving light guide 15. A great variety of combinations is also possible here. A uniform arrangement and distribution of transmitting light guides and receiving light guides 14 and 15, respectively, is likewise possible. Their configuration and arrangement are governed by the intended use.

If appropriate, the number of transmitting light guides 14 can also exceed the number of receiving light guides 15, in order to ensure adequate illumination of a measuring area. The probe housing 11 with the measuring probe 10 can dip into the interior of the receptacle 1 steplessly or in increments.

Figures 3, 4:
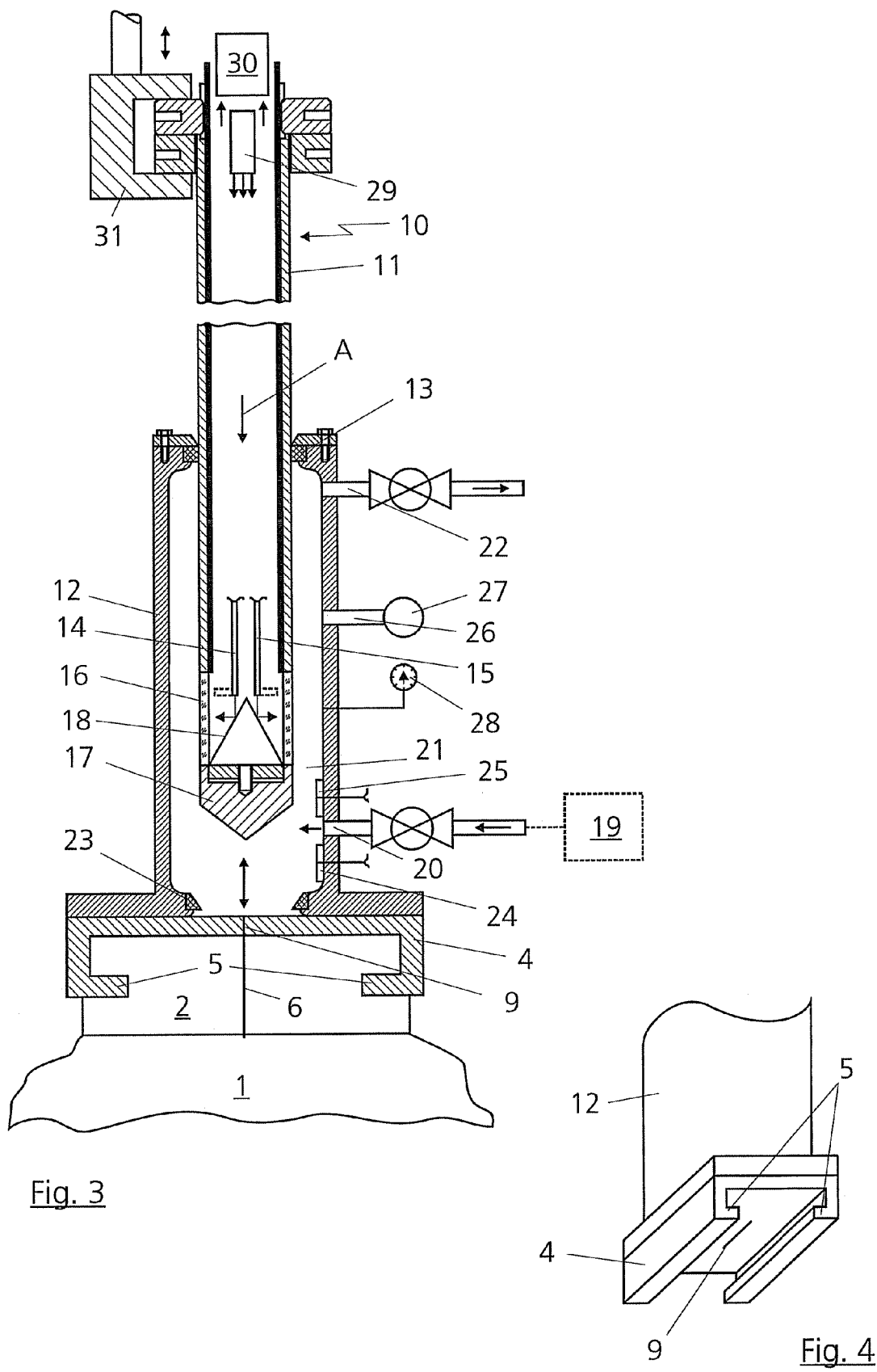
FIG. 3 is a side cross-sectional view of a preferred embodiment of the apparatus of the invention shown with its docking element attached to the coupling element of a receptacle of the type shown in FIG. 1 and having its probe shown in a retracted position.
FIG. 4 is a perspective view showing a detail of the docking element at the lower region of the apparatus according to FIG. 3.

FIG. 3 shows the position of the measuring probe 10 in which it is located in a retracted position not yet pushed into receptacle 1.

Starting from the retracted position of the measuring probe 10 illustrated in FIG. 3, said measuring probe is pushed, for the purpose of measuring and analyzing into the interior of the receptacle 1 with the region of the probe housing 11 in which one or more measuring windows 16 are located. To this end, the measuring probe 10 is displaced together with the probe housing 11 in an axial direction, in a direction (A) of the arrow, in the interior of the guide housing 12. Since the sealing cap 17 on the front end face of the probe housing 11 has a wedge shape or is of conical design, and also the docking element 4, provided with the slit 9, is designed to be elastically compliant, the measuring probe 10 can dip into the interior of the receptacle 1 owing to an appropriate widening of the slit 9 and of the slit 6 of the coupling element 2.

The axial dipping of the measuring probe 10 takes place to such an extent that the measuring window or windows 16 are located in the interior of the receptacle 1, and appropriate measurements and analyzes can be carried out.

Depending on the length of the probe housing 11, the measuring probe 10 can dip into the receptacle 1 to an appropriate depth, and thus provide a profile of the product against height. On the basis of the elasticity of the docking element 4 and of the coupling element 2 together with the elastic expansion of the two slits 6 and 9, sealing also simultaneously takes place during the measuring method, since the slit walls can bear sealingly against the probe housing 11. Moreover, a sealing ring 23 also serves for a reliable seal.

After an analysis, it is also possible in the position illustrated in FIG. 3 to perform cleaning (not illustrated in more detail) of the measuring window or windows 16 and of the outer wall of the probe housing 11 by a flushing device 19 (not illustrated in more detail). Starting from the flushing device 19, flushing medium is introduced for this purpose via one or more channels 20, arranged in the guide housing 12, into an intermediate region 21 between the inner wall of the guide housing 12 and the outer wall of the probe housing 11, and also discharged again therefrom via one or more outlet channels 22.

Figure 5:
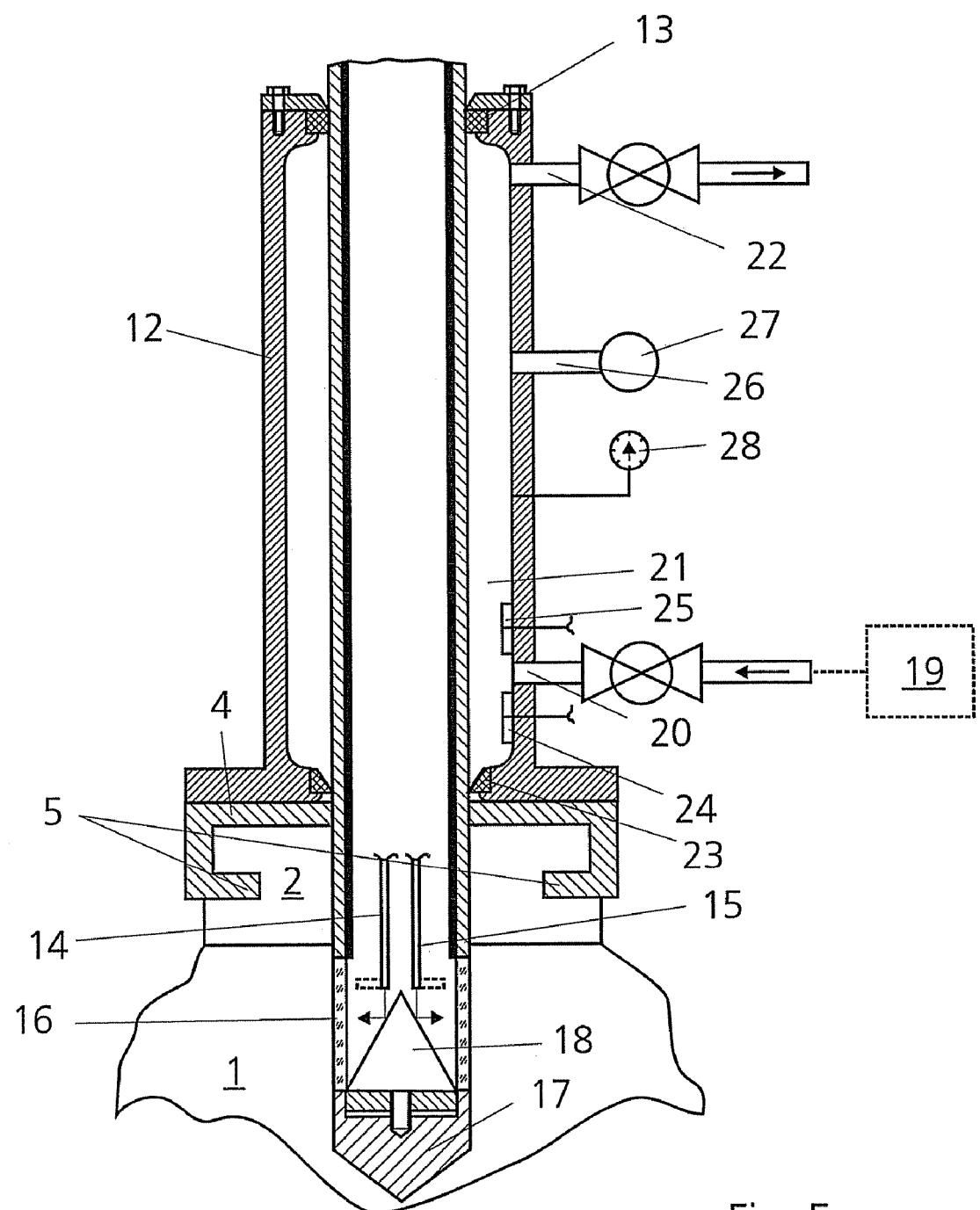
FIG. 5 is a side cross sectional view of the embodiment of FIG. 3 shown with its probe in an extended position inserted into the receptacle.

As may be seen from the positionings as illustrated in FIGS. 3 and 5, it is also possible to clean the measuring window or windows 16 as early as when the sealing cap 17 arranged on the end face of the probe housing 11 is still located as sealing element at least partially in the interior of the receptacle, and thus a seal still remains in relation to the interior of the receptacle 1. On the other hand, in this position the region of the measuring window or windows 16 is located outside the receptacle 1, and can in this way be cleaned.

At the same time, it is also possible in the position in accordance with FIG. 3 to carry out, if required, further measuring methods with the aid of specific reference material, for example by means of a white balancing device. For this purpose, a white standard calibration element 24 (not illustrated in more detail) can be provided, for example, an identical or another sensor undertaking the comparison with a black standard calibration element in a second calibration position. It is likewise also possible to use a calibration device 25 (correspondingly not illustrated in more detail), which just like the white balancing device 24 is provided in the guide housing 12, to carry out calibrating operations (not explained in any more detail). In principle, however, such measuring methods and calibration operations are generally known.

Product from the interior of the receptacle 1 which adheres to the outer wall of the probe housing 11 can be scraped off at the sealing part 23, designed as a scraper ring, during the retraction of the measuring probe 10.

The interspace 21 can also be connected via a pressure connection 26 to a compressed air source 27. By adding compressed gas to the interspace 21 drying can be achieved after cleaning of the measuring window 16 and of the remaining region of the probe housing 11. When, in addition, a connection to a gas pressure testing device 28 is also present, a pressure test of the interspace 21 can also be carried out for tightness.

Also to be seen in principle from FIG. 3 is a light source 29 which is connected to the transmitting light guides 14.

An optical fibre collector 30 can be provided for receiving the light or the beams returned via the receiving light guides 15.

Instead of a beam deflecting device for example with the deflecting mirror 18 illustrated, the transmitting light guides 14 and the receiving light guides 15 can also be deflected from their axial directions into a radial direction, or obliquely, in their lower regions, that is to say in the region of the measuring window 16, such that the beams or the light are or is passed on directly and also received directly (see dashed illustration of the diversion of a transmitting and a receiving light guide, respectively, in FIG. 3).

Also illustrated in FIG. 3 is an actuator 31 by means of which the measuring probe 10 can be dipped into the receptacle 1, and can also be partially or fully removed from it again.

It goes without saying that the guide housing 12 and the probe housing 11 need not be of circular design, but can, if required, also have—seen in cross section—an oval, polygonal or else some other shape.

It goes without saying that the coupling element 2 and also the docking element 4 need not be of completely elastic design and neither need the slots necessarily be opened by the actions of forces from outside according to the arrows in FIG. 2. All that is essential is for the two elements to be elastic at least in the region of the slits 6 and 9 in such a way that the slits 6 and 9 can be expanded elastically to form a gap through which the measuring probe 10 can be pushed in, and this is also particularly facilitated by the wedge shape or conical shape of the sealing cap 17.

Since the measuring probe 10 is located in the interior of the guide housing 12 and is sealed off from the outside, there is also no need for the docking element 4 necessarily to be sealed by a closed slit 9 in the nonactivated state, but it can, if appropriate, also have an opening of the size of the diameter of the measuring probe housing 11. When the analyzing apparatus is connected to the coupling element 2 via the docking element 4, the sealing cap 17 need then only expand the gap 6 of the coupling element 2 in order to produce an environmentally tight connection between the measuring probe 10 and the interior of the receptacle 1.

In the retracted position of the measuring probe 10, system tests can be undertaken in accordance with generally known test standards. Apart from calibration, system checks are consequently also possible, and apart from cleaning, drying of the measuring probe 10 or the probe housing 11 is also possible.

While the foregoing constitute preferred embodiments of the invention according to the best mode presently contemplated by the inventors of making and carrying out the invention, it is to be understood that the invention is not limited to the particulars described above. In light of the present disclosure, various alternative embodiments and modifications will be made apparent to those skilled in the art. Accordingly, it is to be recognized that changes can be made without departing from the scope of the invention as particularly pointed out and distinctly claimed in the appended claims as properly construed to include all legal equivalents.

What is claimed is:

1. An apparatus for carrying out environmentally isolated analysis of contents of the interior of a receptacle of the type having a sealable coupling element, said apparatus, comprising:
    (a) a guide housing which at least partially encloses a space inside said guide housing;
    (b) a docking element coupled to said guide housing, said docking element being removably attachable to the coupling element to form a sealed connection between said space inside said guide housing and at least a portion of the coupling element, and
    (c) a probe having (i) a probe housing which includes at least one window of a solid material transmissive of radiant energy, (ii) at least one transmitting element disposed to transmit radiant energy from said probe, and (iii) at least one detecting element disposed to receive radiant energy by way of said window; at least a portion of said probe housing being received within said space inside said guide housing, said probe housing and said guide housing being displaceable relative to one another between at least (i) a retracted position at which said probe is clear of the coupling element when said docking element is attached to the coupling element, and (ii) an extended position at which said probe penetrates the coupling element to expose said at least one window to the interior of the receptacle when said docking element is attached to the coupling element to permit analysis of the contents of the receptacle to be carried out based on said radiant energy received by said at least one detecting element.

2. An apparatus according to claim 1, further comprising at least one seal disposed between said probe housing and said guide housing.

3. An apparatus according to claim 1, wherein said probe housing includes a circumferential wall and said at least one window is located in at least a portion of said circumferential wall.

4. An apparatus according to claim 3, wherein said probe further comprises a sealing cap coupled to said probe housing, said sealing cap being sealably engageable to form a seal between said interior space of said guide housing and the interior of the receptacle so as to permit introduction of a cleaning medium into said interior space without contaminating the contents of the interior of the receptacle even if said docking element is attached to the coupling element and said probe is not in said retracted position.

5. An apparatus according to claim 4, wherein said sealing cap is either wedge-shaped or conical.

6. An apparatus according to claim 3, wherein said guide housing is provided with a sealing part which engages said probe housing while said probe is in said extended position to form a seal between said space inside said guide housing and the interior of the receptacle when said probe is in said extended position.

7. An apparatus according to claim 6, wherein said sealing part acts to remove clinging material from the probe housing as the probe is displaced from said extended position to said retracted position.

8. An apparatus according to claim 1, further comprising a flushing device for cleaning said window.

9. An apparatus according to claim 8, wherein said flushing device comprises a flushing medium chamber located within at least a portion of said space inside said guide housing.

10. An apparatus according to claim 9, wherein said probe housing has an end terminated by a sealing cap which can be positioned inside said flushing medium chamber for cleaning.

11. An apparatus according to claim 1, wherein said guide housing is provided with at least one gas connection for feeding a dry gas into said interior space inside said guide housing.

12. An apparatus according to claim 1, further comprising at least one reference element operably disposed inside said guide housing.

13. An apparatus according to claim 1, further comprising at least one test element operably disposed inside said guide housing.

14. An apparatus according to claim 13, wherein said at least one test element comprises at least one calibrating device.

15. An apparatus according to claim 14, wherein said calibrating element comprises at least one white standard calibrating element.

16. An apparatus according to claim 1, wherein said transmitting element comprises at least one transmitting light guide.

17. An apparatus according to claim 16, wherein at least one said transmitting light guide has an end portion which is angularly deflected toward said window.

18. An apparatus according to claim 1, wherein said detecting element comprises at least one receiving light guide.

19. An apparatus according to claim 18, wherein at least one said receiving light guide has an end portion which is angularly deflected toward said window.

20. An apparatus according to claim 1 further comprising at least one beam deflecting device located inside said probe housing in a radiation path in common with said window.

21. An apparatus according to claim 20, wherein said beam deflecting device comprises at least one mirror located such that radiation axially incident upon said mirror from one of said transmitting light guides is deflected in an at least approximately radial direction.

22. An apparatus according to claim 21, wherein said at least one mirror comprises a plurality of circumferentially disposed reflecting surfaces.

23. An apparatus according to claim 22, wherein said the at least one mirror has a substantially pyramidal shape.

24. An apparatus according to claim 22, wherein said at least one mirror has a substantially conical shape.

25. An apparatus according to claim 22, wherein said beam deflecting device is pivotable.

26. An apparatus according to claim 20, wherein said beam deflecting device is rotatable.

27. An apparatus according to claim 1, wherein at least a portion of said measuring window is formed from a material selected from the group consisting of sapphire and quartz.

28. An apparatus according to claim 1, wherein said docking element is provided with an opening through which passes at least a portion of said probe housing.

29. An apparatus according to claim 28, wherein at least a portion of said docking element surrounding said opening is formed of an elastic.

30. An apparatus according to claim 29, wherein said opening comprises a slit.

31. A method for carrying out environmentally isolated analysis of contents of the interior of a receptacle of the type having a sealable coupling element, said method comprising the steps of:
   (a) providing at least one probe having (i) a probe housing which includes at least one window of a solid material transmissive of radiant energy, (ii) at least one transmitting element disposed to transmit radiant energy from said probe, (iii) at least one detecting element disposed to receive radiant energy by way of said window;
   (b) providing a guide housing which at least partially encloses an environmentally isolable space inside said guide housing in which at least a portion of said probe housing is received;
   (c) attaching said guide housing to the coupling element;
   (d) forming a sealed connection between said space inside said guide housing and at least a portion of the coupling element;
   (e) effecting relative displacement between said probe housing and said guide housing from (i) a retracted position at which said probe is clear of the coupling element when said docking element is attached to the coupling element, to (ii) an extended position at which said probe penetrates the coupling element to expose said at least one window to the interior of the receptacle when said docking element is attached to the coupling element.

32. A method according to claim 31, further comprising the steps of:
   (a) at least partially retracting said probe from said extended position, and
   (b) cleaning said window while said probe is in at least partially retracted from said extended position.

33. A method according to claim 32, wherein said cleaning step comprises the step of guiding at least a portion of said housing past a scraper ring which forms a seal between said guide housing and said probe housing.

34. A method according to claim 32, wherein said cleaning step comprises the step of introducing a cleaning medium into said space inside said guide housing.

35. A method according to claim 33, wherein said cleaning step further comprises the step of introducing a cleaning medium into said space inside said guide housing.

36. A method according to one of claims 31 to 35, further comprising the step of calibrating said probe when said probe is in said retracted position.

37. A method according to any of claims 31 to 35, further comprising the step of introducing a dry gas into said space inside said guide housing.

* * * * *